United States Patent
Bohlmann et al.

(10) Patent No.: US 6,790,842 B1
(45) Date of Patent: Sep. 14, 2004

(54) 11β LONG-CHAIN SUBSTITUTED ESTRATRIENES, METHOD FOR THEIR PRODUCTION, PHARMACEUTICAL PREPARATIONS CONTAINING SAID 11β LONG-CHAIN SUBSTITUTED ESTRATRIENES, AND THEIR USE FOR PRODUCING MEDICAMENTS

(75) Inventors: Rolf Bohlmann, Berlin (DE); Nikolaus Heinrich, Berlin (DE); Jorg Kroll, Berlin (DE); Gerhard Sauer, Berlin (DE); Karl-Heinrich Fritzemeier, Berlin (DE); Christa Hegele-Hartung, Mulheim a.d. Ruhr (DE); Jens Hoffmann, Muhlenbeck (DE); Rosemarie Lichtner, Berlin (DE); Ludwig Zorn, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 10/018,429

(22) PCT Filed: Jun. 26, 2000

(86) PCT No.: PCT/EP00/05969
§ 371 (c)(1),
(2), (4) Date: May 7, 2002

(87) PCT Pub. No.: WO01/00652
PCT Pub. Date: Jan. 4, 2001

(30) Foreign Application Priority Data

Jun. 24, 1999 (DE) .......................................... 199 29 715

(51) Int. Cl.$^7$ .......................... A61K 31/58; A61K 31/56; C07J 1/00
(52) U.S. Cl. .......................... 514/176; 514/182; 552/626
(58) Field of Search .......................... 552/626; 514/176, 514/182

(56) References Cited

FOREIGN PATENT DOCUMENTS

| EP | 0384842 A | 8/1990 |
|---|---|---|
| EP | 0850647 A | 7/1998 |
| FR | 2640977 A | 6/1990 |
| WO | WO 9313123 A | 7/1993 |
| WO | WO 9730697 A | 8/1997 |
| WO | WO 9828324 A | 7/1998 |
| WO | WO 9925725 A | 5/1999 |
| WO | WO 0031112 A | 6/2000 |

OTHER PUBLICATIONS

C Lobaccaro et al: Steroidal Affinity Labels of the Estrogen Receptor. 3. Journal of Medicinal Chemistry, US, American Chemical Society. Washington, vol. 40, No. 14, Jul. 4, 1997.

Primary Examiner—Barbara P. Badio
(74) Attorney, Agent, or Firm—Millen, White, Zelano & Branigan, P.C.

(57) ABSTRACT

This invention describes a 11β-long-chain-substituted estratriene of general formula (I), in which $R^{11}$ is a long-chain radical that has a nitrogen atom and optionally a sulfur atom, which in addition can be functionalized in the terminal position with a perfluoroalkyl group or an optionally substituted arly radical. The compound can have antiestrogenic or tissue-selective estrogenic properties and be suitable for the production of pharmaceutical agents.

15 Claims, No Drawings

11β LONG-CHAIN SUBSTITUTED ESTRATRIENES, METHOD FOR THEIR PRODUCTION, PHARMACEUTICAL PREPARATIONS CONTAINING SAID 11β LONG-CHAIN SUBSTITUTED ESTRATRIENES, AND THEIR USE FOR PRODUCING MEDICAMENTS

This application is a 371 of PCT/EP00/05969 filed Jun. 26, 2000.

This invention relates to 11β-long-chain-substituted estratrienes of general formula I

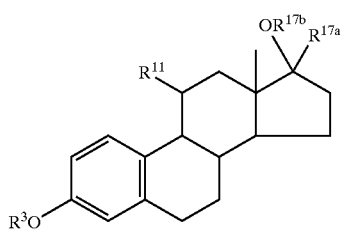

(I)

in which
$R^3$ means a hydrogen atom, a hydrocarbon radical with up to 8 carbon atoms or a radical of partial formula $R^{3'}$—C(O)—, in which $R^{3'}$ means a hydrogen atom or a hydrocarbon radical with up to 8 carbon atoms or a phenyl radical,
$R^{11}$ means a radical of formula —A—B—Z—$R^{20}$, in which
A stands for a direct bond, and
B stands for a straight-chain or branched-chain alkylene, alkenylene or alkinylene group with 4, 5 or 6 carbon atoms, or
A stands for a phenylene radical, and
B stands for a methylene, ethylene, propylene or trimethylene group, or
A stands for a phenylenoxy radical, whereby the latter is bonded via a carbon atom to the 11-carbon atom of the steroid, and
B stands for an ethylene group, and
Z stands for —$NR^{21}$— and $R^{21}$ stands for a $C_1$–$C_3$ alkyl group,
whereby $R^{20}$ means
a hydrogen atom,
a straight-chain or branched-chain alkyl, alkenyl or alkinyl group with up to 10 carbon atoms, whereby if A is a direct bond, $R^{20}$ and $R^{21}$ do not both simultaneously mean methyl, however, and, if A is a phenylenoxy radical, $R^{20}$ and $R^{21}$ do not both simultaneously mean methyl or ethyl in each case, and if A is a phenylenoxy radical and B means an ethylene group, $OR^{17b}$ should not be a hydroxy group and $R^{17a}$ should not be a $C_{1-4}$ alkyl group, and $R^3$ should not be a hydrogen atom,
or one of groupings
—D—$C_nF_{2n+1}$, whereby D is a straight-chain or branched-chain alkylene, alkenylene or alkinylene group with up to 8 carbon atoms and n is an integer from 1 to 8, D-aryl, whereby D has the already indicated meaning, and aryl stands for a phenyl, 1- or 2-naphthyl radical or a heteroaryl radical that is optionally substituted in one or two places,
—L—CH=CF—$C_pF_{2p+1}$, whereby L is a straight-chain or branched-chain alkylene, alkenylene or alkinylene group with up to 7 carbon atoms and p is an integer from 1 to 7,
whereby in the three cases above in D or L, a methylene group can be replaced by a sulfur atom, a sulfone group or a sulfoxide group,
—D—O—$(CH_2)_q$-aryl, whereby D and aryl have the already indicated meanings, and q is 0, 1, 2 or 3,
—D—O—$(CH_2)_r$—$C_nF_{2n+1}$, whereby D and n have the already indicated meanings, and r stands for an integer from 1 to 5,
whereby in addition in all relevant cases above, $R^{21}$ together with D with the inclusion of the nitrogen atom can then form a pyrrolidine ring that is substituted in 2- or 3-position, or
if A is a direct bond or a phenylene radical, $R^{20}$ and $R^{21}$ with the nitrogen atom to which they are bonded form a saturated or unsaturated heterocyclic compound with 5 or 6 chain links, which optionally contains one or two additional heteroatoms, selected from nitrogen, oxygen and sulfur, and optionally is substituted,
whereby if A is a phenylene radical and B is a trimethylene radical, $R^{21}$ and $R^{20}$ do not form a methyl or ethyl group, or, together with the nitrogen atom to which they are bonded, do not form a pyrrolidine or and
$R^{17a\alpha}$in α- or β-position means a hydrogen atom, a $C_{1-5}$ alkyl, a $C_{2-5}$ alkenyl or a $C_{2-5}$ alkinyl group or a trifluoromethyl group, or together with the radical $OR^{17b}$ means a keto-oxygen atom, and
$R^{17b}$ means a hydrogen atom or a radical of partial formula $R^{17'}$—C(O)—, in which $R^{17'}$ means a hydrogen atom or a hydrocarbon radical with up to 8 carbon atoms.

As $R^3$, the substituted estratrienes according to the invention preferably have a hydrogen atom. The hydroxy group, however, can also be etherified with a straight-chain or branched-chain, saturated or unsaturated hydrocarbon radical with up to 8 carbon atoms, such as, e.g., a methyl, ethyl, propyl, isopropyl, butyl, isobutyl, tert-butyl, pentyl, isopentyl, neopentyl, heptyl, hexyl or octyl radical or esterified with an acyl radical $R^{3'}$—C(O)—, in which $R^{3'}$ is a hydrogen atom or a hydrocarbon radical with up to 8 carbon atoms or a phenyl radical.

A hydrogen atom or a radical of partial formula $R^{17'}$—C(O)— can stand for substituents $R^{17b}$, in which $R^{17'}$ is a hydrogen atom or a hydrocarbon radical with up to 8 carbon atoms. A hydrogen atom is preferred for $R^{17b}$. The hydrocarbon radical can have the meaning of, for example, a methyl, ethyl, propyl, isopropyl; butyl, isobutyl, tert-butyl, pentyl, isopentyl, neopentyl, heptyl, hexyl or octyl radical. In addition, the substituent —$OR^{17b}$ can be in α- or β-position. The β-position is preferred.

$R^{17b}$ can mean a hydrogen atom, a straight-chain or branched $C_{1-5}$ alkyl radical, such as, for example, a methyl, ethyl, propyl, isopropyl, butyl, isobutyl, tert-butyl, pentyl, isopentyl, neopentyl radical, a straight-chain or branched $C_{2-5}$ alkenyl radical, such as, for example, an ethenyl, 1-propenyl, 2-propenyl, isopropenyl, 1-butenyl, 2-butenyl, 3-butenyl, 1-ethyl-ethenyl, 2-ethylethenyl, 1-methyl(1-propenyl), 1-methyl(2-propenyl) radical, or a straight-chain or branched $C_{2-5}$ alkinyl radical, such as, for example, an ethinyl, 1-propinyl, 2-propinyl, 1-butinyl, 2-butinyl, 3-butinyl, 3-methyl (1-butinyl)-, 1-methyl (3-butinyl) radical and a trifluoromethyl radical.

$R^{17b}$ preferably means a hydrogen atom, a $C_{2-3}$ alkenyl radical, a $C_{2-3}$ alkinyl radical or a trifluoromethyl group.

$R^{17a}$ especially preferably means a hydrogen atom, a methyl group, an ethenyl radical, an ethinyl radical or a trifluoromethyl group.

In addition, the radical $R^{17a}$ can be in α- or β-position. The α-position is preferred for $R^{17a}$.

Another meaning for $R^{17b}$ together with $OR^{17a}$ is a keto-oxygen atom. This meaning is to be preferred before any other substitution in 17-position.

In the compounds of general formula I according to the invention, A stands for a direct bond, a phenylene or phenylenoxy radical, whereby the latter is connected via one of its carbon atoms to carbon atom 11 of the steroid skeleton.

An aryl radical that optionally can be substituted is a phenyl, 1- or 2-naphthyl radical in terms of this invention; the phenyl radical is preferred. Unless expressly indicated otherwise, aryl also always includes a heteroaryl radical. Examples of a heteroaryl radical are the 2-, 3- or 4-pyridinyl, the 2- or 3-furyl, the 2- or 3-thienyl, the 2- or 3-pyrrolyl, the 2-, 4- or 5-imidazolyl, the pyrazinyl, the 2-, 4- or 5-pyrimidinyl or the 3- or 4-pyridazinyl radical.

If $R^{20}$ and $R^{21}$ with the nitrogen atom, to which they are bonded, contain a saturated or unsaturated heterocycle with 5 or 6 chain links, which optionally contains one or two additional heteroatoms that are selected from nitrogen, oxygen and sulfur, this is especially a pyrrolidine, piperidine, morpholine or piperazine ring As substituents for the aryl, heteroaryl, aralkyl and heteroarylalkyl radicals, for example, a methyl-, ethyl-, propyl-, trifluoromethyl-, pentafluoroethyl-, trifluoromethylthio-, methoxy-, ethoxy-, nitro-, cyano-, halogen-(fluorine, chlorine, bromine, iodine), hydroxy-, amino-, mono($C_{1-8}$ alkyl)- or di($C_{1-8}$ alkyl)amino, whereby both alkyl groups are identical or different, di(aralkyl)amino, whereby both aralkyl groups are identical or different (for aralkyl, see above at $R^{20}$ and $R^{31}$) or the 1-methoxyacetylamino radical can be mentioned.

The sulfur atom in the side chain can be present as a single sulfur bridge (sulfide), as sulfone or sulfoxide.

As specific side chains,

—$(CH_2)_5N(CH_3)$—$(CH_2)_3$—S—$(CH_2)_3C_2F_5$
—$(CH_2)_5NH$—$(CH_2)_3$—S—$(CH_2)_3C_2F_5$
—$(CH_2)_5N(CH_3)$—$(CH_2)_3$—S—$CH_2$-2-Pyridyl
—$(CH_2)_5N(CH_3)$—$(CH_2)_3$—SO—$CH_2$-2-Pyridyl
—$(CH_2)_5N(CH_3)$—$(CH_2)_3$—S—$CH_2$-p-$CF_3$-Phenyl
—$(CH_2)_5N(CH_3)$—$(CH_2)_3$—SO—$CH_2$-p-$CF_3$-Phenyl
—$(CH_2)_5$-[2-Pyrrolidin-1-yl]—$CH_2$—S-p-$CF_3$-Phenyl
—$(CH_2)_5$-[2-Pyrrolidin-1-yl]—$CH_2$—SO-p-$CF_3$-Phenyl
p-Phenylen-$(CH_2)_2$—$N(CH_3)$—$(CH_2)_3$—S—$(CH_2)_3C_2F_5$
p-Phenylen-$(CH_2)_2$—$N(CH_3)$—$(CH_2)_3$—SO—$(CH_2)_3$-$C_2F_5$
p-Phenylen-$(CH_2)_2$—$N(CH_3)$—$(CH_2)_3$—S—$CH_2$-2-Pyridyl
p-Phenylen-$(CH_2)_2$—$N(CH_3)$—$(CH_2)_3$—SO—$CH_2$—2-Pyridyl
p-Phenylen-$(CH_2)_2$—$N(CH_3)$—$(CH_2)_3$—S—$CH_2$-p-$CF_3$-Phenyl
p-Phenylen-$(CH_2)_2$—$N(CH_3)$—$(CH_2)_3$—SO—$CH_2$-p-$CF_3$-Phenyl
—$(CH_2)_5N(CH_3)(CH_2)_3C_2F_5$
—$(CH_2)_5N(CH_3)(CH_2)_6C_2F_5$
—$(CH_2)_5N(CH_3)(CH_2)_7C_2F_5$
—$(CH_2)_5N(CH_3)(CH_2)_8C_2F_5$
—$(CH_2)_6N(CH_3)(CH_2)_6C_2F_5$
—$(CH_2)_6N(CH_3)(CH_2)_7C_2F_5$
—$(CH_2)_6N(CH_3)(CH_2)_8C_2F_5$
—$(CH_2)_5N(CH_3)(CH_2)_2C_4F_9$
—$(CH_2)_5N(CH_3)(CH_2)_3C_6F_{13}$
—$(CH_2)_5N(CH_3)(CH_2)_3C_8F_{17}$
—$(CH_2)_5N(CH_3)(CH_2)_6C_4F_9$
—$(CH_2)_5N(CH_3)(CH_2)_6C_6F_{13}$
—$(CH_2)_5N(CH_3)(CH_2)_6C_8F_{17}$
—$(CH_2)_5N(CH_3)H$
—$(CH_2)_5N(CH_3)(CH_2)_9H$
—$(CH_2)_5N(CH_3)CH_2CH=CF$—$C_2F_5$
—$(CH_2)_5N(CH_3)CH_2CH=CF$—$C_3F_7$
—$(CH_2)_5N(CH_3)CH_2CH=CF$—$C_5F_{11}$
—$(CH_2)_5N(CH_3)CH_2CH=CF$—$C_7F_{15}$
—$(CH_2)_5$-1-Pyrrolidinyl
—$(CH_2)_5N(CH_3)(CH_2)_3OPhenyl$
—$(CH_2)_5N(CH_3)(CH_2)_3OBenzyl$
—$(CH_2)_5N(CH_3)(CH_2)_3O(CH_2)_3C_2F_5$
—$(CH_2)_5N(CH_3)(CH_2)_3CH(CH_3)_2$
—$(CH_2)_5N(CH_3)(CH_2)_3$-Pyridyl
—$(CH_2)_5N(CH_3)(CH_2)_3$-Phenyl
—$(CH_2)_5N(CH_3)(CH_2)_2$-p-Tolyl
—$(CH_2)_5N(CH_3)(CH_2)_2$-p-Ethoxyphenyl
—$(CH_2)_5N(CH_3)(CH_2)_3$-p-Tolyl⁻
—$(CH_2)_5N(CH_3)(CH_2)_3$-p-Chlorphenyl
—$(CH_2)_5N(CH_3)(CH_2)_3$—O—$CH_2$-Phenyl
—$(CH_2)_5N(CH_3)(CH_2)_2$—O-p-Br-Phenyl
—$(CH_2)_5N(CH_3)(CH_2)_2$—O-p-$CF_3$-Phenyl can be mentioned.

[Key:]
—$(CH_2)_5$-[2-Pyrrolidin-1-yl]- . . . =$(CH_2)_5$-[2-pyrrolidine-1-yl]- . . . p-Phenylen- . . . =p-phenylene- . . .

This invention relates to the following compounds, i.a.:

11β-[5-(Methyl(3-[(4,4,5,5,5-pentafluoropentyl)sulfanyl]-propyl}amino)pentyl]estra-1,3,5(10)-triene-3,17β-diol 11β-(5-{3-[(4;4,5,5,5-pentafluoropentyl)sulfanyl]propyl-amino}pentyl)estra-1,3,5(10)-triene-3,17β-diol 11β-[5-(methyl{3-[(2-pyridylmethyl)sulfanyl]propyl}-amino)pentyl]estra-1,3,5(10)-triene-3,17β-diol 11β-[5-(methyl{3-[(2-pyridylmethyl)sulfinyl]propyl}-amino)pentyl]estra-1,3,5(10)-triene-3,17β-diol 11β-[5-(methyl{3-[4-(trifluoromethyl)benzylsulfanyl]-propyl}amino)pentyl]estra-1,3,5(10)-triene-3,17β-diol 11β-[5-(methyl{3-[4 -(trifluoromethyl)benzylsulfinyl]-propyl}amino)pentyl]estra-1,3,5(10)-triene-3,17β-diol 11β-{5-[(2S)-2-{[4-(trifluoromethyl)phenyl]sulfanyl-methyl}pyrrolidin-1-yl]pentyl}estra-1,3,5(10)-triene-3,17β-diol 11β-{5-[(2S)-2-{[4-(trifluoromethyl)phenyl]sulfinyl-methyl}pyrrolidin-1-yl]pentyl}estra-1,3,5(10)-triene-3,17β-diol 11β-{4-[2-(methyl{3-[(4,4,5,5,5-pentafluoropentyl)sulfanyl]-propyl}amino)ethyl]phenyl}-estra-1,3,5(10)-triene-3,17β-diol 11β-{4-[2-(methyl{3-[(4,4,5,5,5-pentafluoropentyl)sulfinyl]-propyl}amino)ethyl]phenyl}estra-1,3,5(10)-triene-3,17β-diol 11β-{4-[2-(methyl{3-[(2-pyridylmethyl)sulfanyl]propyl}-amino)ethyl]phenyl}estra-1,3,5(10)-triene-3,17β-diol 11β-{4-[2-(methyl{3-[(2-pyridylmethyl)sulfinyl]propyl}-amino)ethyl]phenyl}estra-1,3,5(10)-triene-3,17β-diol 11β-{4-[2-(methyl{3-[4-(trifluoromethyl)benzylsulfanyl]-propyl}amino)ethyl]phenyl}estra-1,3,5(10)-triene-3,17β-diol 11β-{4-[2-(methyl{3-[4-(trifluoromethyl)benzylsulfinyl]-propyl}amino)ethyl]phenyl}estra-1,3,5(10)-triene-3,17β-diol 11β-{5-[methyl-(8,8,9,9,9-pentafluoro-nonyl)-amino]-pentyl}-estra-1,3,5(10)-triene-3,17β-diol 11β-{5[methyl-nonyl-amino]-pentyl}-estra-1,3,5(10)-triene-3,17β-diol 11β-{5-[methyl-(9,9,10,10,10-pentafluoro-decyl)-amino]-pentyl}-estra-1,3,5(10)-triene-3,17β-diol 11β-{6-[methyl-(8,8,9,9,9-pentafluoro-nonyl)amino]-hexyl}-estra-1,3,5(10)-triene-3,17β-diol 11β-{6-[methyl-(9,9,10,10,10-pentafluoro-decyl)-amino]-hexyl}-estra-1,3,5(10)-triene-3,17β-diol 11β-(5-(methyl-amino)-pentyl)-estra-1,3,5(10)-triene-3,17β-diol 11β-(5-pyrrolidin-1-yl-pentyl)-estra-1,3,5(10)-triene-3,17β-diol 11β-{5-[methyl-(4,4,5,5,5-pentafluoro-pentyl)-amino]-pentyl}-estra-1,3,5(10)-triene-3,17β-diol 11β-{5-[methyl-(4,4,5,5,6,6,7,7,8,8,9,9,9-tridecafluoro-nonyl)-amino]-pentyl}-estra-1,3,5(10)-triene-3,17β-diol 11β-{5-[(4,4,5,5,6,6,7,7,8,8,9,9,10,10,11,11,11-heptadecafluoro-undecyl)-methyl-amino]-pentyl}-estra-1,3,5(10)-triene-3,17β-diol 11β-{5-[methyl-(3,3,4,4,5,5,6,6,6-nonafluoro-hexyl)-amino]-pentyl}-estra-1,3,5(10)-triene-3,17β-diol 11β-{5-[methyl-(7,7,8,8,8-pentafluoro-octyl)-amino]-pentyl}-estra-1,3,5(10)-triene-3,17β-diol 11β-{6-[methyl-(7,7,8,8,8-pentafluoro-octyl)-amino]-hexyl}-estra-1,3,5(10)-triene-3,17β-diol 11β-{5-[methyl-(7,7,8,8,9,9,10,10,10-nonafluoro-decyl)-amino]-pentyl}-estra-1,3,5(10)-triene-3,17β-diol 11β-{5-[methyl-(7,7,8,8,9,9,10,10,11,11,12,12,12-tridecafluoro-dodecyl)-amino]-pentyl}-estra-1,3,5(10)-triene-3,17β-diol 11β-{5-[(7,7,8,8,9,9,10,10,11,11,12,12,13,13,14,14,14-heptadecafluoro-tetradecyl)-methyl-amino]-pentyl}-estra-1,3,5(10)-triene-3,17β-diol 11β-{5-[(3,4,4,5,5,5-hexafluoro-pent-2-enyl)-methyl-amino]-pentyl}-estra-1,3,5(10)-triene-3,17β-diol 11β-{5-[(3,4,4,5,5,6,6,7,7,8,8,8-dodecafluoro-oct-2-enyl)-methyl-amino]-pentyl}-estra-1,3,5(10)-triene-3,17β-diol 11β-{5-[(3,4,4,5,5,6,6,7,7,8,8,9,9,10,10,10-hexadecafluoro-dec-2-enyl)-methyl-amino]-pentyl}-estra-1,3,5(10)-triene-3,17β-diol 11β-{5-[methyl-(3-phenoxy-propyl)-amino]-pentyl}-estra-1,3,5(10)-triene-3,17β-diol 11β-{5-[(3-benzyloxy-propyl)-methyl-amino]-pentyl}-estra-1,3,5(10)-triene-3,17β-diol 11β-{5-[N-methyl-N-3-(4,4,5,5,5-pentafluoropentyloxy)-propylamino]-pentyl}-estra-1,3,5(10)-triene-3,17β-diol 11β-[9-(4,4,5,5,5-pentafluoropentylsulfinyl)-nonyl]-estra-1,3,5(10)-triene-3,17β-diol 11β-{5-[methyl-(2-p-tolyl-ethyl)-amino]-pentyl}-estra-1,3,5(10)-triene-3,17β-diol 11β-(5-{[2-(4-ethoxy-phenyl)-ethyl]-methyl-amino}-pentyl)-estra-1,3,5(10)-triene-3,17β-diol 11β-{5-[methyl-(3-phenyl-propyl)-amino)-pentyl}-estra-1,3,5(10)-triene-3,17β-diol 11β-{5-[methyl-(3-pyridin-3-yl-propyl)-amino]-pentyl}-estra-1,3,5(10)-triene-3,17β-diol 11β-{5-[methyl-(3-p-tolyl-propyl)-amino]-pentyl}-estra-1,3,5(10)-triene-3,17β-diol 11β-(5-{[3-(4-chloro-phenyl)-propyl]-methyl-amino}-pentyl)-estra-1,3,5(10)-triene-3,17β-diol 11β-(5-{[3-(4-ethoxy-phenyl)-propyl]-methyl-amino}-pentyl)-estra-1,3,5(10)-triene-3,17β-diol 11β-{5-[methyl-(4-methyl-pentyl)-amino]-pentyl}-estra-1,3,5(10)-triene-3,17β-diol In addition to these compounds of general formula I, this invention also relates to their physiologically compatible addition salts with organic and inorganic acids, pharmaceutical preparations that contain these compounds of general formula I inclusive of the addition salts, as well as their use for the production of pharmaceutical agents.

Inorganic and organic acids, as are known to one skilled in the art for the formation of physiologically compatible salts, are suitable for the formation of acid addition salts. As addition salts with acids, especially hydrochlorides, hydrobromides, acetates, citrates, oxalates, tartrates and methanesulfonates can be cited.

The compounds of general formula I represent compounds with strong antiestrogenic action and with surprising possible oral uses.

The compounds according to the invention are either pure antiestrogens or so-called partial antagonists, i.e., antiestrogens with partial estrogenic action such as tamoxifen or raloxifen. In contrast to the tamoxifen, their agonistic, estrogenic action is expressed in a tissue-selective manner in the case of partial antagonists of general formula I. In particular, the agonistic action occurs in bone, in the cardiovascular system and in the central nervous system. In particular, no action or only slightly agonistic action occurs in the uterus.

Compounds with antiestrogenic properties, i.e., substances with inhibiting actions compared to estrogens, have already been described extensively.

Estratrienes that carry a β-position substituent in 11-position and that also have, i.a., antiestrogenic action, are known from, for example, the following patent applications: WO 98/28324, EP-A 0 850 647, EP-A 0 629 635, WO 93/13123, EP-A 0 558 416, EP-A 0 471 612, EP-A 0 384 842, EP-B 0 097 572, WO/99 25725.

In addition, the steroid derivatives that are known from EP 0 138 504 B1 can be mentioned. The 7α-[9-(4,4,5,5,5-pentafluoropentylsulfinyl)-n-nonyl]-estra-1,3,5(10)-triene-3,17β-diol is currently under clinical development for hormone-dependent tumors (breast cancer).

Pharmaceutical compositions that contain sex steroid inhibitors and that have a steroidal skeleton that has a 7α-side chain in the case of the simultaneous presence of at least one other substituent in 14-, 15- or 16-position are the subject matter of EP-A 0 376 576.

Antiestrogenically active estratrienes that can carry an 11β-fluorine atom and carry an a-position side chain in 7-position, which has an amino group and a sulfur group and that is functionalized in the terminal position, are described in WO 98/07740.

The compounds according to the invention are compounds with stronger antiestrogenic action after peroral administration.

The antiuterus growth test in infant rats, s.c. and p.o. (test on antiestrogenic action in-vivo) confirms the antiestrogenic action of the compounds according to the invention. The test is performed as described below:

Uterus Growth Test in Infant Rats (Antiestrogenic Action) Principle of the Method In rodents, the uterus reacts to the administration of estrogens with an increase in weight (both proliferation and water retention). This growth can be inhibited in a dose-dependent manner by simultaneous administration of compounds that have an antiestrogenic action.

Execution of the Test

Animals:

Infant female rats weighing 35–45 g at the beginning of the test, 5–6 animals per dose.

Formulation and Administration of the Substances:

For the p.o. administration, the substances are dissolved in 1 part ethanol (E) and made up with 9 parts peanut oil (E Ö).

Test Batch

The young rats just dropped by the mothers are delivered for acclimation one day before the beginning of treatment and immediately supplied with food—right in the cage. The treatment is then carried out once daily over 3 days in combination with 0.5 µg of estradiol benzoate (EB). EB is always administered subcutaneously (s.c.), while the test substance is administered p.o. (perorally). 24 hours after the last administration, the animals are weighed, killed and the uteri are removed. The moist weight (less contents) is determined from the prepared uteri.

Controls

Negative control: Vehicle (E/Ë), 0.2 ml/animal/day

Positive control: 0.5 µg of EB/0.1 ml/animal/day

Evaluation

The average values with standard deviation (X+SD) and the significance of the differences in the control group (EB) in the Dunnett Test (p<0.05) are determined for each group from the relative organ weights (mg/100 g of body weight). The calculation of the inhibition (in %) compared to the EB-control is carried out with a program. The relative actions of the test substances are determined by co-variance analysis and regression analysis.

As pure antiestrogens for the purposes of this invention, those compounds of general formula I that show no action or, in the best case, only slightly agonistic action, in the in-vitro test on estrogenic action can be considered.

By means of the method described below, the estrogenic effect of the compounds according to the invention on the bones can be determined. In the case of selectively estrogenically active compounds, protective effects on the bones are observed with comparable dosages, while on the uterus, no stimulation, or in the best case, only slight stimulation, is noted.

Bone Studies

Method

Female rats that are three months old are ovariectomized and treated once daily with the test compound immediately after the operation for 28 days. The administration is carried out subcutaneously in castor oil/benzyl benzoate or arachis oil/ethanol. The animals are sacrificed on the day after the last administration, and femurs, tibia as well as the uteri are removed. The uteri are weighed, mounted and worked up for histological studies. The determination of the bone density is carried out ex vivo on prepared long bones via pQCT (Quantitative Computer Tomography). The measurements are made at a distance of 5–7 mm from the ball of the joint at the distal femur or the proximal tibia.

As an alternative, the action on the bones by measuring out the trabecular bone surface area of the secondary spongiosa on histologic preparations of the distal femur or the proximal tibia is noted. The result is expressed as the proportion, in percent, of the trabecular bone surface area to the measured total bone surface area (TB/BV). The bone density that is measured via QCT and the trabecular bone surface area that is determined at the histologic section correlate well with one another. A comparison of the two measurement variables is therefore permissible.

The transition between the pure antiestrogens and the partial agonists, the tissue-selective estrogens, is seamless. Compounds that have a slightly agonistic action can also be used in the indications that are mentioned below for pure antiestrogens:

The compounds according to the invention, especially if they are pure antiestrogens, are suitable for treatment of estrogen-dependent diseases, for example breast cancer (second-line treatment of tamoxifen-resistant breast cancer; for adjuvant treatment of breast cancer instead of tamoxifen), endometrial cancer, prostate cancer, prostatic hyperplasia, anovulatory infertility and melanoma.

In addition, the pure antiestrogens of general formula I can be used as components in the products that are described in EP 346 014 B1, which contain an estrogen and a pure antiestrogen, specifically for simultaneous, sequential or separate use for selective estrogen therapy of peri- or post-menopausal women. The compounds of general formula I, especially if these are pure antiestrogens, can be used together with antigestagens (competitive progesterone antagonists) for the treatment of hormone-dependent tumors (EP 310 542 A).

Other indications in which the compounds of the general formula can be used are male hair loss, diffuse alopecia, alopecia that is caused by chemotherapy as well as hirsutism (Hye-Sun Oh and Robert C. Smart, Proc. Natl. Acad. Sci. USA, 93 (1996) 12525–12530).

In addition, the compounds of general formula I can be used for the production of medications for treating endometriosis and endometrial carcinomas.

The compounds of general formula I can also be used for the production of pharmaceutical compositions for male and female birth control (male birth control: DE-A 195 10 B62.0).

The compounds of general formula I with tissue-selective partial estrogenic action can be used primarily for prophylaxis and treatment of osteoporosis and for the production of preparations for substitution therapy in pre-, peri- and post-menopause (HRT=hormone replacement therapy) (Black; L. J.; Sato, M.; Rowley, E. R.; Magee, D. E.; Bekele, A.; Williams; D. C.; Cullinan, C. J.; Bendele, R.; Kauffman, R. F.; Bensch, W. R.; Frolik, C. A.; Termine, J. D. and Bryant, E. U.: Raloxifene [LY 139481 HCl] Prevents Bone Loss and Reduces Serum Cholesterol without Causing Uterine Hypertrophy in Ovariectomized Rats; J. Clin. Invest. 93: 63–69, 1994).

The invention also relates to pharmaceutical preparations that contain at least one compound of general formula I (or physiologically compatible addition salts with organic and inorganic acids of them) and the use of these compounds for the production of pharmaceutical agents, especially for treating estrogen-dependent diseases and tumors and pharmaceutical agents for hormone replacement therapy (HRT).

The compounds according to the invention and the acid addition salts are suitable for the production of pharmaceutical compositions and preparations. As active ingredients, the pharmaceutical compositions or pharmaceutical agents contain one or more of the compounds according to the invention or their acid addition salts, optionally mixed with other pharmacologically or pharmaceutically active substances. The production of the pharmaceutical agents is carried out in a known way, whereby the known and commonly used pharmaceutical adjuvants and other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), pages 91B and ff.; issued by Czetsch-Lindenwald, Hilfsstoffe für Pharmazie und angrenzende Gebiete [Adjuvants for Pharmaceutics and Related Fields]; Pharm. Ind. Issue 2, 1961, pages 72 and ff.; Dr. H. P. Fiedler, Lexikon der Hilfsstoffe für Pharmazie, Kosmetik und angrenzende Gebiete [Dictionary of Adjuvants for Pharmaceutics, Cosmetics and Related Fields] Cantor KG, Aulendorf in Württemberg 1971.

The compounds can be administered orally or parenterally, for example intraperitoneally, intramuscularly, subcutaneously or percutaneously. The compounds can also be implanted in the tissue. The amount of the compounds to be administered varies within a wide range and can cover any effective amount. Based on the condition to be treated and the type of administration, the amount of the administered compound can be 0.1–25 mg/kg of body weight, preferably 0.5–5 mg/kg of body weight, per day. In humans, this corresponds to a daily dose of 5 to 1250 mg. The preferred daily dosage in humans is 50 to 200 mg. This is true especially for tumor therapy.

For oral administration, capsules, pills, tablets, coated tablets, etc., are suitable. In addition to the active ingredient, the dosage units can contain a pharmaceutically compatible vehicle, such as, for example, starch, sugar, sorbitol, gelatin, lubricant, silicic acid, talc, etc. The individual dosage units for oral administration can contain, for example, 5 to 500 mg of active ingredient.

To achieve better bio-availability of the active ingredient, the compounds can also be formulated as cyclodextrin clathrates. For this purpose, the compounds are reacted with α-, β- or γ-cyclodextrin or derivatives thereof (PCT/EP95/02656).

For parenteral administration, the active ingredients can be dissolved or suspended in a physiologically compatible diluent. As diluent, very frequently oils with or without the addition of a solubilizer, a surfactant, a suspending agent or emulsifier are used. Examples of oils that are used are olive oil, peanut oil, cottonseed oil, soybean oil, castor oil and sesame oil.

The compounds of general formula I can also be formulated in the form of a solution that is determined for oral administration and that in addition to the active compound of general formula I contains a) a pharmaceutically compatible oil and/or
b) a pharmaceutically compatible lipophilic surfactant and/or
c) a pharmaceutically compatible hydrophilic surfactant and/or
d) a pharmaceutically compatible water-miscible solvent.

In this respect, reference is made in addition to WO 97/21440.

The compounds can also be used in the form of a depot injection or an implant preparation, which can be formulated in such a way that a delayed release of active ingredient is made possible.

As inert materials, implants can also contain, for example, biodegradable polymers or synthetic silicones such as, for example, silicone gum. In addition, the active ingredients can be embedded in, for example, a patch for percutaneous administration.

For the production of intravaginal systems (e.g., vaginal rings) or intrauterine systems (e.g., pessaries, spirals) that are loaded with active compounds of general formula I, various polymers such as, for example, silicone polymers, ethylene vinyl, acetate, polyethylene or polypropylene are suitable.

The compounds according to the invention can be produced as described below. The examples below are used for a more detailed explanation of the invention. Other compounds of general formula I can be obtained by an analogous procedure using analogous reagents in the data contained in the examples.

Side chains $R^{11}$ that do not contain any sulfur groups can be created analogously to the corresponding 7α-position side chains of the compounds that are described in PCT/EP98/08470, whereby the 11β-(5-chloropentyl)estra-1,3,5 (10)-triene-3,17β-diol that is described here in Example 1d or the 11β-(5-iodopentyl)estra-1,3,5(10)-triene-3,17β-diol that is described in Example 3a is now to be taken as a starting material.

A thio bridge in the side chain can be oxidized with sodium periodate to form sulfoxide; the sulfones are obtained from the sulfides with a peracid as an oxidizing agent, e.g., m-chloroperbenzoic acid.

The saponification of the ester groupings as well as esterification and etherification of free hydroxy groups is carried out in each case according to established processes of organic chemistry. By observing the varied reactivity of the esterified and free 3- and 17-hydroxy groups, the 3,17-diesters can be cleaved selectively in 3-position, and the 3-hydroxy-17-acyloxy compound can then be additionally functionalized specifically in the 3-position; it is equally possible to esterify or to etherify the 3,17-dihydroxy compound selectively only in the 3-position and then to introduce specifically another radical into the 17-position as already in the 3-position.

The acid addition salts of the compounds of general formula I can also be produced from the compounds of general formula I according to standard processes.

The examples below are used for a more detailed explanation of the invention:

EXAMPLE 1

11β-[5-(Methyl{3-[(4,4,5,5,5-pentafluoropentyl) sulfanyl]-propyl}amino)pentyl]estra-1,3,5(10)-triene-3,17β-diol a) 11β-[5-(tert-Butyldimethylsilyloxy)pentyl]-3,3-(2,2-dimethyltrimethylenedioxy)-5α-estr-9-ene-5,17β-diol 1.82 g of magnesium in 15 ml of absolute tetrahydrofuran is reacted under nitrogen with a solution of 21.1 g of 1-bromo-5-tert-butyldimethylsilyloxypentane [Tetrahedron Letters 1982, 4147–4150] in 40 ml of absolute tetrahydrofuran to form a Grignard reagent. At 0° C., 0.25 g of copper(I) chloride is added, and it is stirred for 15 more minutes, before a solution of 9.36 g of 3,3-(2,2-dimethyltrimethylenedioxy)-5,10α-epoxy-5α-estr-9(11)-en-17β-ol [Neef, G. et al., Tetrahedron, (1993), 49, pp. 833–840)] in 40 ml of absolute tetrahydrofuran is added in drops, such that the internal temperature does not exceed 8° C. After the addition is completed, it is stirred for 90 more minutes while being cooled in an ice bath. For working-up, the reaction mixture is added to saturated ammonium chloride solution while being stirred, extracted three times with ethyl acetate, the combined ethyl acetate phases are washed with saturated sodium chloride solution, dried on sodium sulfate and evaporated to the dry state in a vacuum. Preparative column chromatography on silica gel with hexane/ethyl acetate as an eluant yields 5.02 g of 11β-[5-(tert-butyldimethylsilyloxy)pentyl]-3,3-(2,2-dimethyltrimethylenedioxy)-5α-estr-9-ene-5,17β-diol as a foam.

b) 17β-Hydroxy-11β-(5-hydroxypentyl)estra-4,9-dien-3-one 4.96 g of 11β-[5-(tert-butyldimethylsilyloxy)pentyl]-3,3-(2,2-dimethyltrimethylenedioxy)-5α-estr-9-ene-5,17β-diol in 36 ml of tetrahydrofuran is stirred under nitrogen with 40 ml of glacial acetic acid and 20 ml of water for 3 hours at a bath temperature of 50° C. Then, it is carefully poured onto saturated sodium bicarbonate solution, extracted three times with ethyl acetate, the combined organic phases are washed with saturated sodium chloride solution, dried on sodium sulfate and evaporated to the dry state in a vacuum. By preparative column chromatography on silica gel with hexane/acetone as an eluant, 3.57 g of 17β-hydroxy-11β-(5-hydroxyphenyl)estra-4,9-dien-3-one is obtained as a foam.

c) 11β-(5-Hydroxypentyl)-9ξ-estra-1,3,5(10)-triene-3,17β-diol

A solution of 1.08 g of 17β-hydroxy-11β-(5-hydroxypentyl)estra-4,9-dien-3-one in 19 ml of ethanol is refluxed with 0.19 g of palladium on activated carbon for 20 hours at a bath temperature of 100° C. After cooling, it is filtered on Celite, rewashed with ethyl acetate, the filtrate is evaporated to the dry state and chromatographed on silica gel with hexane/acetone. Recrystallization from methylene chloride results in 0.46 g of 11β-(5-hydroxypentyl)-9ξ-estra-1,3,5(10)-triene-3,17β-diol with a melting point of 152° C.

d) 11β-(5-Chloropentyl)estra-1,3,5(10)-triene-3,17β-diol 426 mg of 11β-(5-hydroxypentyl)-9ξ-estra-1,3,5(10)-triene-3,17β-diol is suspended in 7.2 ml of carbon tetrachloride and 2.4 ml of acetonitrile, mixed with 682 mg of triphenyl-phosphine and stirred for 90 minutes at room temperature. For working-up, the reaction solution is mixed with methylene chloride, washed with saturated sodium bicarbonate solution and saturated sodium chloride solution, dried on sodium sulfate, and concentrated by evaporation in a vacuum. By preparative column chromatography on silica gel with methylene chloride/ethyl acetate, the 9ξ-isomers can be separated. Subsequent crystallization from methylene chloride yields 238 mg of 11β-(5-chloropentyl)estra-1,3,5 (10)-triene-3,17β-diol with a melting point of 159° C.

e) 11β-[5-(Methyl{3-[(4,4,5,5,5-pentafluoropentyl) sulfanyl]-propyl]amino)pentyl]estra-1,3,5(10)-triene-3,17β-diol 189 mg of 11β-(5-chloropentyl)estra-1,3,5(10)-triene-3, 17β-diol is dissolved in 3 ml of dried dimethylformamide, mixed with 598 mg of methyl{3-[(4,4,5,5,5-pentafluoropentyl)-sulfanyl]propyl}amine [DE 196 35 525.7] and stirred for 24 hours at 100° C. under nitrogen. After the reaction mixture is cooled, it is diluted with ethyl acetate, washed once with saturated sodium bicarbonate solution and twice with saturated sodium chloride solution, dried on sodium sulfate and concentrated by evaporation in a vacuum. After preparative column chromatography on silica gel with ethyl acetate/methanol as an eluant, 222 mg of 11β-[5-(methyl{3-[(4,4,5,5,5-pentafluoropentyl)sulfanyl] propyl}-amino)pentyl]estra-1,3,5(10)-triene-3,17β-diol is obtained as a foam $[\alpha]_D^{22}$=+72.1° (c=0.172 in chloroform).

EXAMPLE 2

11β-(5-{3-[(4,4,5,5,5-Pentafluoropentyl)sulfanyl]-propylamino}pentyl)estra-1,3,5(10)-triene-3,17β-diol 98 mg of 11β-(5-chloropentyl)estra-1,3,5(10)-triene-3, 17β-diol is dissolved in 1.5 ml of dried dimethylformamide, mixed with 3 ml of 3-[(4,4,5,5,5-pentafluoropentyl) sulfanyl]-propylamine and stirred for 16 hours under nitrogen at a bath temperature of 80° C. After the reaction solution is cooled, it is diluted with ethyl acetate, washed once with water and twice with saturated sodium chloride solution, dried on sodium sulfate and concentrated by evaporation in a vacuum. Preparative column chromatography on silica gel with methylene chloride/methanol with the addition of ammonia results in 31 mg of 11β-(5-{3-[(4,4,5, 5,5-pentafluoropentyl)sulfanyl]propylamino}pentyl)-estra-1,3,5(10)-triene-3,17β-diol as a foam.

EXAMPLE 3

11β-[5-(Methyl{3-[(2-pyridylmethyl)sulfanyl] propyl)-amino)pentyl]estra-1,3,5(10)-triene-3,17β-diol a) 11β-(5-Iodopentyl)estra-1,3,5(10)-triene-3,17β-diol 1.46 g of 11β-(5-chloropentyl)estra-1,3,5(10)-triene-3, 17β-diol is dissolved in 24 ml of ethylmethylketone, mixed with 1.82 g of sodium iodide and stirred overnight at a bath temperature of 90° C. For working-up, the reaction mixture is added to water, extracted three times with ethyl acetate, washed with sodium thiosulfate solution, dried on magnesium sulfate and concentrated by evaporation in a vacuum. 1.86 g of 11β-(5-iodopentyl)estra-1,3,5(10)-triene-3,17β-diol is obtained as a crude product, which is used in the next reaction without further purification.

b) 11β-[5-(Methyl{3-[(2-pyridylmethyl)sulfanyl] propyl}amino)-pentyl]estra-1,3,5(10)-triene-3,17β-diol 1.0 g of 11β-(5-iodopentyl)estra-1,3,5(10)-triene-3,17β-diol and 2.47 g of methyl{3-[(2-pyridylmethyl)sulfanyl] propyl}amine are dissolved in 21 ml of N-methylpyrrolidone and stirred for 3 hours at 80° C. After the reaction solution is cooled to room temperature, the batch is added to semi-saturated sodium chloride solution, extracted three times with diethyl ether, the combined organic phases are washed with water and saturated sodium chloride solution, dried on magnesium sulfate and concentrated by evaporation in a vacuum. Preparative column chromatography on silica gel with methylene chloride/methanol as an eluant yields 0.69 g of 11β-[5-(methyl{3-[(2-pyridyl-methyl)sulfanyl]propyl}-amino)pentyl]estra-1, 3,5(10)-triene-3,17β-diol as a foam, $[\alpha]_D^{22}$=+62.2° (c=0.519 in chloroform).

EXAMPLE 4

11β-[5-(Methyl{3-[2-pyridylmethyl) sulfinyl] propyl}amino)-pentyl]estra-1,3,5(10)-triene-3,17β-diol 250 mg of 11β[5-(methyl{3-[(2-pyridylmethyl)sulfanyl]-propyl}amino)pentyl]estra-1,3,5(10)-triene-3,17β-diol is dissolved in 8.1 ml of methanol and 0.44 ml of water, mixed with 161 mg of sodium metaperiodate and stirred for 16 hours at room temperature. For working-up, the reaction mixture is added to semi-saturated sodium chloride solution, extracted three times with methylene chloride, the combined organic phases are dried on magnesium sulfate and concentrated by evaporation in a vacuum. Preparative column chromatography on silica gel with methylene chloride/methanol as an eluant yields 53 mg of 11β-[5-(methyl{3-[(2-pyridylmethyl)sulfinyl]propyl}-amino)pentyl]estra-1,3,5(10)-triene-3,17β-diol as a foam.

$[\alpha]_D^{22}$=+56.9° (c=0.501 in chloroform)

EXAMPLE 5

11β-[5-(Methyl{3-[4-(trifluoromethyl)benzylsulfanyl]-propyl}amino)pentyl]estra-1,3,5(10)-triene-3,17β-diol 839 mg of 11β-(5-iodopentyl)estra-1,3,5(10)-triene-3,17β-diol and 1.42 g of methyl{3-[4-(trifluoromethyl)benzylsulfanyl]-propyl}amine are dissolved in 18 ml of N-methylpyrrolidone and stirred for 90 minutes at a bath temperature of 80° C. After the reaction solution is cooled to room temperature, the batch is added to semi-saturated sodium chloride solution, extracted three times with diethyl ether, the combined organic phases are washed with water and saturated sodium chloride solution, dried on magnesium sulfate and concentrated by evaporation in a vacuum. Preparative column chromatography on silica gel with methylene chloride/methanol as an eluant yields 0.94 g of 11β-[5-(methyl{3-[4-(trifluoromethyl)benzylsulfanyl]propyl}amino)pentyl]estra-1,3,5(10)-triene-3,17β-diol as a foam, $[\alpha]_D^{22}$=+75.0° (c=0.5 in chloroform).

EXAMPLE 6

11β-[5-(Methyl{3-[4-(trifluoromethyl)benzylsulfinyl]-propyl}amino)pentyl]estra-1,3,5(10)-triene-3,17β-diol 630 mg of 11β-[5-(methyl{3-[4-(trifluoromethyl)benzylsulfanyl]propyl}amino)pentyl]estra-1,3,5(10)-triene-3,17β-diol is dissolved in 17.4 ml of methanol and 0.95 ml of water, mixed with 329 mg of sodium metaperiodate and stirred at room temperature for 16 hours. For working-up, the reaction mixture is added to semi-saturated sodium chloride solution, extracted three times with methylene chloride, the combined organic phases are dried on magnesium sulfate and concentrated by evaporation in a vacuum. Preparative column chromatography on silica gel with methylene chloride/methanol as an eluant yields 216 mg of 11β-[5-(methyl{3-[4-(trifluoromethyl)benzylsulfinyl]propyl}amino)pentyl]estra-1,3,5(10)-triene-3,17β-diol as a foam, $[\alpha]_D^{22}$=+54.10 (c=0.501 in chloroform).

EXAMPLE 7

11β-{5-[(2S)-2-{[4-(Trifluoromethyl)phenyl]sulfanylmethyl}-pyrrolidin-1-yl]pentyl}estra-1,3,5(10)-triene-3,17β-diol 820 mg of 11β-(5-iodopentyl)estra-1,3,5(l0)-triene-3,17β-diol and 458 mg of (S)-2-{[4-(trifluoromethyl)phenyl]sulfanyl-methyl}pyrrolidine are dissolved in 16 ml of N-methylpyrrolidone and stirred for 3 hours at a bath temperature of 90° C. After the reaction solution is cooled to room temperature, the batch is added to semi-saturated sodium chloride solution, extracted three times with ethyl acetate, the combined organic phases are washed three times with water, dried on magnesium sulfate and concentrated by evaporation in a vacuum. Preparative column chromatography on silica gel with methylene chloride/methanol as an eluant yields 561 mg of 11β-{5-[(2S)-2-}[4-(trifluoromethyl)-phenyl]sulfanylmethyl}pyrrolidin-1-yl]pentyl}estra-1,3,5(10)-triene-3,17β-diol as a foam, $[\alpha]_D^{22}$=+33.1° (c=0.5195 in chloroform).

EXAMPLE 8

11β-{5-[(2S)-2-{[4-(Trifluoromethyl)phenyl]sulfinylmethyl}-pyrrolidin-1-yl]pentyl}estra-1,3,5(10)-triene-3,17β-diol 975 mg of 11β-(5-iodopentyl)estra-1,3,5(10)-triene-3,17β-diol and 540 mg of (S)-2-{[4-(trifluoromethyl)phenyl]sulfinyl-methyl}pyrrolidine are dissolved in 19 ml of N-methylpyrrolidone and stirred for 3 hours at a bath temperature of 90° C. After the reaction solution is cooled to room temperature, the batch is added to semi-saturated sodium chloride solution, extracted three times with ethyl acetate, the combined organic phases are washed twice with water, dried on magnesium sulfate, and concentrated by evaporation in a vacuum. Chromatography on silica gel with methylene chloride/methanol yields 222 mg of 11β-{5-[-(2S)-2-{[4-(trifluoromethyl)phenyl] sulfinyl-methyl}pyrrolidine-1-yl]pentyl}-estra-1,3,5(10)-triene-3,17β-diol as a foam. $[\alpha]_D^{22}$=+42.6° (c=0.5145 in chloroform).

EXAMPLE 9

11β-{4-[2-(Methyl{3-[(4,4,5,5,5-pentafluoropentyl)sulfanyl]-propyl}amino)ethyl]phenyl}estra-1,3,5(10)-triene-3,17β-diol a). 11β-{4-[2-(tert-Butyldimethylsilyloxy)ethyl]phenyl}-3,3-(2,2-dimethyltrimethylene-dioxy)-5α-estr-9-ene-5,17β-diol 1.94 g of magnesium chips is introduced under nitrogen into 15 ml of absolute tetrahydrofuran and mixed with about 2.5 g of 1-bromo-4-[2-(tert-butyldimethylsilyloxy)ethyl]benzene in 4 ml of absolute tetrahydrofuran as well as a spatula tip full of iodine. After the reaction is started, the residual 22.8 g of 1-bromo-4-[2-(tert-butyl-dimethylsilyloxy)ethyl]benzene is added in drops to 36 ml of absolute tetrahydrofuran, and after the addition is completed, it is stirred for 1 hour at 80° C. Then, it is cooled to 0° C., mixed with 267 mg of copper(I) chloride and stirred for 30 more minutes under cold conditions. Then, 10 g of 3,3-(2,2-dimethyltrimethylenedioxy)-5,10α-epoxy-5α-estr-9(11)-en-17β-ol is added in drops while being cooled in an ice bath in such a way that the internal temperature does not exceed +8° C. After 2 hours of stirring at 0° C., the reaction mixture is added to saturated ammonium chloride solution, extracted three times with ethyl acetate, washed with saturated sodium chloride solution, dried on magnesium sulfate and concentrated by evaporation in a vacuum. Preparative column chromatography on silica gel with hexane/ethyl acetate as an eluant results in 11.97 g of 11β-{4-[2-(tert-butyldimethylsilyloxy)ethyl]phenyl}-3,3-(2,2-dimethyltrimethylenedioxy)-5α-estr-9-ene-5,17β-diol.

b) 17β-Hydroxy-11β-[4-(2-hydroxyethyl)phenyl]estra-4,9-dien-3-one 11.27 g of 11β-{4-[2-(tert-butyldimethylsilyloxy)ethyl]-phenyl}-3,3-(2,2-dimethyl-trimethylenedioxy)-5α-estr-9-ene-5,17β-diol is dissolved in 70 ml of tetrahydrofuran, mixed with 86 ml of glacial acetic acid as well as 43 ml of water and stirred for 1 hour at a bath temperature of 50° C. After the cooling, the reaction solution is carefully added to ice-cold sodium bicarbonate solution, extracted three times with ethyl acetate, washed with saturated sodium chloride solution, dried on magnesium sulfate and concentrated by evaporation in a vacuum. After preparative column chromatography on silica gel with hexane/acetone as an eluant, 6.73 g of 17-hydroxy-11β-[4-(2-hydroxyethyl)phenyl]estra-4,9-dien-3-one is obtained as a foam.

c) 11β-[4-(2-Chloroethyl)phenyl]-17β-hydroxyestra-4,9-dien-3-one 6.32 g of 17β-hydroxy-11β-[4-(2-hydroxyethyl)phenyl] estra-4,9-dien-3-one is dissolved in 160 ml of methylene chloride, mixed with 7.65 g of triphenylphosphine and 16.1 ml of perchloro-acetone and stirred for 1 hour at room temperature. Then, the reaction mixture is concentrated by evaporation in a vacuum and chromatographed on silica gel with hexane/ethyl acetate as well as methylene chloride/methanol as an eluant. 3.19 g of 11β-[4-(2-chloroethyl)phenyl]-17β-hydroxyestra-4,9-dien-3-one is obtained as a foam.

d) 11β-[4-(2Chloroethyl)phenyl]estra-1,3,5(10)-triene-3,17β-diol

A solution of 2.94 g of 11β-[4-(2-chloroethyl)phenyl]-17β-hydroxyestra-4,9-dien-3-one in 70 ml of ethanol is refluxed with 458 mg of palladium on activated carbon for 5 hours at a bath temperature of 100° C. After cooling to room temperature, it is filtered on Celite, rewashed with ethanol and concentrated by, evaporation in a vacuum. Preparative column chromatography on silica gel with hexane/ethyl acetate as an eluant yields 522 mg of 11β-[4-(2-chloroethyl)phenyl]estra-1,3,5(10)-triene-3,17β-diol as a foam.

e) 11β-[4-(2-Iodoethyl)phenyl]estra-1,3,5(10)-triene-3,17β-diol 312 mg of 11β-[4-(2-chloroethyl)phenyl]estra-1,3,5(10)-triene-3,17β-diol is dissolved in 5 ml of ethylmethylketone, mixed with 341 mg of sodium iodide and stirred for 16 hours at 90° C. For working-up, the reaction mixture is added to water, extracted three times with ethyl acetate, washed with thiosulfate solution, dried on magnesium sulfate and concentrated by evaporation in a vacuum. 382 mg of 11β-[4-(2-iodoethyl)phenyl]estra-1,3,5(10)-triene-3,17β-diol is obtained as a crude product, which is used in the next stage without further purification.

f) 11β-{4-[2-(Methyl{3-[(4,4,5,5.,5-pentafluoropentyl)sulfanyl]-propyl}amino)ethyl]phenyl}estra-1,3,5(10)-triene-3,17β-diol 382 mg of 11β-[4-(2-iodoethyl)phenyl]estra-1,3,5(10)-triene-3,17β-diol and 603 mg of methyl{3-[(4,4,5,5,5-pentafluoropentyl)sulfanyl]propyl}amine are dissolved in 7.5 ml of N-methylpyrrolidone and stirred for 150 minutes at a bath temperature of 90° C. After the reaction solution is cooled to room temperature, the batch is added to dilute sodium chloride solution, extracted three times with diethyl ether, the combined organic phases are washed with water and saturated sodium chloride solution, dried on magnesium sulfate and concentrated by evaporation in a vacuum. Preparative column chromatography on silica gel with methylene chloride/methanol as an eluant yields 180 mg of 11β-{4-[2-(methyl{3-[(4,4,5,5,5-pentafluoropentyl)-sulfanyl]-propyl}amino)ethyl]phenyl}estra-1,3,5(10)-triene-3,17β-diol as a foam, $[\alpha]_D^{22}$=−14.4° (c=0.502 in chloroform).

EXAMPLE 10

11β-{4-[2-(Methyl{3-[(4,4,5,5,5-pentafluoropentyl) sulfinyl]-propyl}amino)ethyl]phenyl}estra-1,3,5 (10)-triene-3,17β-diol 205 mg of 11β-[4-(2-chloroethyl)phenyl]estra-1,3,5(10)-triene-3,17β-diol and 633 mg of methyl{3-[(4,4,5,5,5-pentafluoropentyl)sulfinyl]propyl}amine are dissolved in 5 ml of dimethylformamide, and stirred for 5 hours at a bath temperature of 90° C. and for 16 hours at room temperature. For working-up, the batch is added to semi-saturated sodium chloride solution, extracted three times with ethyl acetate, washed twice with water, dried on magnesium sulfate and concentrated by evaporation in a vacuum. The residue is chromatographed on silica gel with methylene chloride/methanol as an eluant. 54 mg of 11β-{4-[2-(methyl{3-[(4,4,5,5,5-pentafluoropentyl)sulfinyl]propyl}-amino)ethyl]-phenyl}estra-1,3,5(10)-triene-3,17β-diol is obtained as a foam, $[\alpha]_D^{22}$=−12.9° (c=0.509 in chloroform).

EXAMPLE 11

11β-{4-[2-(Methyl{3-[(2-pyridylmethyl)sulfanyl] propyl}amino)-ethyl]phenyl}estra-1,3,5(10)-triene-3,17β-diol a) 11β-[4-(2-Hydroxyethyl)phenyl]estra-1,3,5(10)-triene-3,17β-diol A solution of 11.7 g of 17β-hydroxy-11β-[4-(2-hydroxyethyl)phenyl]estra-4,9-dien-3-one in 295 ml of methanol is stirred with 8.54 g of palladium hydroxide on activated carbon (20%) and 2.16 g of magnesium oxide for 5 hours at a bath temperature of 70° C. After cooling, it is filtered on Celite, washed with methanol and concentrated by evaporation in a vacuum. The residue is chromatographed on silica gel with hexane/acetone as an eluant. 4.54 g of 11β-[4-(2-hydroxyethyl)phenyl]estra-1,3,5(10)-triene-3,17β-diol is obtained as a foam, $[\alpha]_D^{22}$=−175.5° (c=0.502 in pyridine).

b) 11β-[4-(2-Chloroethyl)phenyl]estra-1,3,5(10)-triene-3,17β-diol 4.50 9 of 11β-[4-(2-hydroxyethyl)phenyl]estra-1,3,5(l0)-triene-3,17β-diol is dissolved in 114 ml of methylene chloride and mixed in succession with 5.45 g of triphenylphosphine and 11.5 ml of perchloroacetone. Then, it is stirred for 90 minutes at room temperature. For working-up, the reaction mixture is concentrated by evaporation in a vacuum and chromatographed on silica gel with methylene chloride/methanol as an eluant. 4.02 g of 11β-[4-(2-chloroethyl) phenyl]estra-1,3,5(10)-triene-3,17β-diol is obtained as a foam, $[\alpha]_D^{22}$=+10.70° (c=0.503 in chloroform).

c) 11β-[4-(2-Iodoethyl)phenyl]estra-1,3,5(10)-triene-3,17β-diol 411 mg of 11β-[4-(2-chloroethyl)phenyl]estra-1,3,5(10)-triene-3,17β-diol is dissolved in 6.5 ml of ethylmethylketone, mixed with 449 mg of sodium iodide and stirred for 16 hours at 90° C. For working-up, the reaction mixture is added to dilute sodium chloride solution, extracted three times with ethyl acetate, washed with thiosulfate solution, dried on magnesium sulfate and concentrated by evaporation in a vacuum. 479 mg of 11β-[4-(2-iodoethyl)phenyl]estra-1,3,5(10)-triene-3,17β-diol is obtained as a crude product, which is used in the next stage without further purification.

d) 11β-{4-[2-(Methyl{3-](2-pyridylmethyl)sulfanyl] propyl}amino)-ethyl]phenyl}estra-1,3,5(10)-triene-3,17β-diol 470 mg of 11β-[4-(2-iodoethyl)phenyl]estra-1,3,5(10)-triene-3,17β-diol and 554 mg of methyl{3-[(2-pyridylmethyl)sulfanyl]-propyl}amine are dissolved in 9 ml of N-methylpyrrolidone and stirred for 2 hours at 90° C. After the reaction solution is cooled to room temperature, the batch is added to semi-saturated sodium chloride solution, extracted three times with diethyl ether, the combined organic phases are washed with water, dried on magnesium sulfate and concentrated by evaporation in a vacuum. Preparative column chromatography on silica gel with methylene chloride/methanol as an eluant yields 93 mg of 11β-{4-[2-(methyl{3-[(2-pyridylmethyl)sulfanyl]propyl}amino)-ethyl]phenyl}estra-1,3,5(10)-triene-3,17β-diol as a foam, $[\alpha]_D^{22}=-31.8°$ (c=0.513 in chloroform).

EXAMPLE 12

11β-{4-[2-(Methyl{3-[(2-pyridylmethyl)sulfinyl]propyl}amino)-ethyl]phenyl}estra-1,3,5(10)-triene-3,17β-diol 68 mg of 11β-{4-[2-(methyl{3-[(2-pyridylmethyl)sulfanyl]-propyl}amino)ethyl]phenyl}estra-1,3,5(10)-triene-3,17β-diol is dissolved in 2 ml of methanol and 0.12 ml of water, mixed with 28 mg of sodium metaperiodate and stirred for 16 hours at room temperature. For working-up, the reaction mixture is added to semi-saturated sodium chloride solution, extracted three times with methylene chloride, washed with saturated sodium chloride solution, dried on magnesium sulfate and concentrated by evaporation in a vacuum. The residue is purified by means of preparative thin-layer chromatography with methylene chloride/methanol with the addition of ammonia as a mobile solvent. 31 mg of 11β-{4-[2-(methyl{3-[(2-pyridylmethyl)-sulfinyl]propyl}amino)ethyl]phenyl}estra-1,3,5(10)-triene-3,17β-diol is obtained as a foam, $[\alpha]_D^{22}=-33.3°$ (c=0.51 in chloroform).

EXAMPLE 13

11β-{4-[2-(Methyl{3-[4-(trifluoromethyl)benzylsulfanyl]-propyl}amino)ethyl]phenyl}estra-1,3,5(10)-triene-3,17β-diol 466 mg of 11β-[4-(2-iodoethyl)phenyl]estra-1,3,5(10)-triene-3,17β-diol and 359 mg of methyl{3-[4-(trifluoromethyl)benzyl-sulfanyl]propyl}amine are dissolved in 9 ml of N-methyl-pyrrolidone and stirred for 4 hours at a bath temperature of 40° C. After the reaction solution is cooled to room temperature, the batch is added to semi-saturated sodium chloride solution, extracted three times with diethyl ether, the combined organic phases are washed with saturated sodium chloride solution, dried on magnesium sulfate and concentrated by evaporation in a vacuum. Preparative column chromatography on silica gel with methylene chloride/methanol as an eluant yields 256 mg of 11β-{4-[2-(methyl{3-[4-(trifluoromethyl)benzylsulfanyl]propyl}-amino)ethyl]phenyl}-estra-1,3,5(10)-triene-3,17β-diol as a foam, $[\alpha]_D^{22}=-20.2°$ (c=0.505 in chloroform).

EXAMPLE 14

11β-{4-[2-(Methyl{3-[4-(trifluoromethyl)benzylsulfinyl]propyl}-amino)ethyl]phenyl}estra-1,3,5(10)-triene-3,17β-diol 100 mg of 11β-{4-[2-(methyl{3-[4-(trifluoromethyl)benzyl-sulfanyl]propyl}amino) ethyl]-phenyl}estra-1,3,5(10)-triene-3,17β-diol is dissolved in 2.6 ml of methanol and 0.15 ml of water, mixed with 36 mg of sodium metaperiodate, and stirred for 4 hours at room temperature. For working-up, the reaction mixture is added to semi-saturated sodium chloride solution, extracted three times with methylene chloride, washed with saturated sodium chloride solution, dried on magnesium sulfate and concentrated by evaporation in a vacuum. The residue is purified by means of preparative thin-layer chromatography with methylene chloride/methanol with the addition of ammonia as a mobile solvent. 48 mg of 11β-{4-[2-(methyl{3-[4-(trifluoromethyl)-benzylsulfinyl]propyl}amino)ethyl]phenyl}estra-1,3,5(10)-triene-3,17β-diol is obtained as a foam, $[\alpha]_D^{22}=-28.8°$ (c=0.511 in chloroform).

Production of the Reagents

3-[(4,4,5,5,5-Pentafluoropentyl)sulfanyl]propylamine 25 g of S-(4,4,5,5,5-pentafluoropentyl)thioacetate [Singh, S. M. et al., Tet. Lett., (1994), 35, pp. 9141–9144] is introduced at 0° C. into 250 ml of absolute acetonitrile and mixed drop by drop with 39.2 ml of a 30% sodium methylate solution. Stirring is continued for 15 minutes under cold conditions, before 23.2 g of 3-bromopropylamine hydrobromide is introduced in portions. Then, it stirred for one more hour at 0° C. The reaction mixture is then added to water, extracted three times with diethyl ether, washed neutral, dried on magnesium sulfate and concentrated by evaporation. After preparative column chromatography on silica gel with methylene chloride/methanol with the addition of ammonia as an eluant, 22.54 g of 3-[(4,4,5,5,5-pentafluoropentyl)sulfanyl]propylamine is obtained.

Methyl{3-[(2-pyridylmethyl)sulfanyl]propyl}amine a) S-(2-pyridylmethyl)thioacetate 10.0 g of 2-(Chloromethyl)pyridine hydrochloride is introduced into 100 ml of acetone, mixed with 14.0 g of potassium thioacetate and refluxed for 2 hours at 80° C. For working-up, the reaction mixture is diluted with ethyl acetate and added to water. It is extracted three times with ethyl acetate, the combined organic phases are washed with saturated sodium bicarbonate solution and with saturated sodium chloride solution, dried on magnesium sulfate and concentrated by evaporation in a vacuum. After preparative column chromatography on silica gel with hexane/ethyl acetate as an eluant, 9.78 g of S-(2-pyridylmethyl)thioacetate is obtained.

b) 2-[(3-Chloropropyl)sulfanylmethyl]pyridine 9.78 g of S-(2-pyridylmethyl)thioacetate in 90 ml of absolute methanol is mixed drop by drop with 10.9 ml of a 30% methanolic sodium methylate solution while being cooled in an ice bath, and after the addition is completed, it is stirred for 20 more minutes. Then, 8.6 ml of 1-bromo-3-chloropropane is added in drops at 4° C. and stirred for two more hours under cold conditions and for one more hour at room temperature. Then, the reaction mixture is added to water, extracted three times with ethyl acetate, the combined organic phases are washed with saturated sodium chloride solution, dried on magnesium sulfate and concentrated by evaporation in a vacuum. Preparative column chromatography on silica gel with hexane/ethyl acetate as an eluant yields 11.7 g of 2-[(3-chloropropyl)sulfanylmethyl]-pyridine.

c) Methyl{3-[(2pyridylmethyl)sulfanyl]propyl}amine 5.85 g of 2-[(3-chloropropyl)sulfanylmethyl]pyridine in 33.5 ml of tetrahydrofuran is mixed with 11.7 g of sodium iodide in a pressure vessel. Then, 17.05 g of methylamine is condensed at −20° C. and heated overnight in a pressure vessel at a bath temperature of 50° C. After the reaction vessel was opened at −20° C., it is allowed to come to room-temperature to allow excess methylamine to evaporate. The reaction solution is added to dilute sodium chloride solution, extracted three times with methylene chloride, the combined organic phases are washed with saturated sodium chloride solution, dried on magnesium sulfate and concentrated by evaporation in a vacuum. 5.7 g of methyl{3-[(2-pyridylmethyl)sulfanyl]propyl}-amine is obtained as a crude product.

Methyl{3-[4-(trifluoromethyl)benzylsulfanyl]propyl}amine a) 1-[(3-Bromopropyl)sulfanylmethyl]-4-(trifluoromethyl)benzene 25.0 g of 4-(trifluoromethyl)benzyl bromide is introduced into 84 ml of acetonitrile, mixed with 8.3 ml of trimethylene sulfide and stirred for 48 hours at room temperature. Then, the reaction mixture is evaporated to the dry state and chromatographed on silica gel with hexane/methylene chloride. 29.47 of 1-[(3-bromopropyl)sulfanyl-methyl]-4-(trifluoromethyl)benzene is obtained as an oil.

b) Methyl{3-[4-(trifluoromethyl)benzylsulfanyl]propyl}amine 18.8 g of methylamine is condensed at −20° C. in a solution of 10.0 g of 1-[(3-bromopropyl)sulfanylmethyl]-4-(trifluoromethyl)-benzene in 37.0 ml of tetrahydrofuran, and it is stirred overnight at room temperature in a pressure vessel. After the pressure vessel was opened at −20° C., it is allowed to come to room temperature to allow excess methylamine to evaporate. The reaction solution is added to dilute sodium chloride solution, extracted three times with methylene chloride, the combined organic phases are washed with saturated sodium chloride solution, dried on magnesium sulfate and concentrated by evaporation in a vacuum. 8.32 g of methyl{3-[4-(trifluoromethyl)benzylsulfanyl]propyl}amine is obtained as a crude product.

1-Bromo-4-[2-(tert-butyldimethylsilyloxy)ethyl]benzene 70 g of 2-(4-bromophenyl)ethanol is dissolved in 350 ml of absolute tetrahydrofuran and mixed with 4.97 g of imidazole. Then, 55 g of tert-butyldimethylsilyl chloride in 230 ml of absolute tetrahydrofuran is added in drops and stirred for 90 minutes at room temperature. For working-up, the reaction mixture is added to ice water, extracted three times with diethyl ether, washed with water, dried on magnesium sulfate and concentrated by evaporation in a vacuum. Preparative column chromatography on silica gel with hexane/ethyl acetate as an eluant yields 111 g of 1-bromo-4-[2-(tort-butyldimethyl-silyloxy)ethyl]benzene as a clear oil.

(S)-2-{[4-(Trifluoromethyl)phenyl]sulfanylmethyl}pyrrolidine a) (S)-tert-Butyl-2-{[4-(trifluoromethyl)phenyl]sulfanylmethyl}-pyrrolidine-1-carboxylate 1.93 ml of a 30% sodium methylate solution is slowly added in drops at 0° C. under inert gas to a solution that consists of 1.4 g of 4-(trifluoromethyl)thiophenol in 15 ml of absolute acetone. After the addition is completed, it is stirred for 30 more minutes under cold conditions, before 1.85 g of (S)-tert-butyl-2-(bromomethyl)pyrrolidine-1-carboxylate [Katzenellenbogen, J. A. et al.; J. Med. Chem., (1994), 37, pp. 928–937] is added in drops to 5 ml of absolute acetone. Then, it is stirred for 30 more minutes under cold conditions and for 12 hours at room temperature. For working-up, the reaction mixture is added to water, extracted three times with diethyl ether, washed twice with saturated sodium chloride solution, dried on magnesium sulfate and concentrated by evaporation in a vacuum. Preparative column chromatography on silica gel with hexane/ethyl acetate as an eluant yields 1.8 g of (S)-tert-butyl-2-{[4-(trifluoromethyl)-phenyl]sulfanylmethyl}pyrrolidine-1-carboxylate as an oil.

b) (S)-2-{[4-(Trifluoromethyl)phenyl]sulfanylmethyl}pyrrolidine 920 mg of (S)-tert-butyl-2-{[4-(trifluoromethyl)phenyl)-sulfanylmethyl{pyrrolidine-1-carboxylate is added to a mixture, cooled to 0° C., that consists of 7.2 ml of trifluoroacetic acid, 0.22 ml of triisopropylsilane and 0.30 ml of water, and it is stirred for 1 hour at 0° C. Then, the reaction is set at pH 10 with 10% potassium hydroxide solution, extracted three times with methylene chloride, washed with saturated sodium chloride solution, dried on magnesium sulfate and concentrated by evaporation in a vacuum. 458 mg of (S)-2-{[4-(trifluoromethyl)-phenyl]sulfanylmethyl}-pyrrolidine is obtained as a crude product.

(S)-2-{[4-(Trifluoromethyl)phenyl]sulfinylmethyl}pyrrolidine a) (S)-tert-Butyl-2-{[4-(trifluoromethyl)phenyl]sulfinylmethyl}-pyrrolidine-1-carboxylate 1.0 g of (S)-tert-butyl-2-{[4-(trifluoromethyl)phenyl]-sulfanylmethyl}pyrrolidine-1-carboxylate is dissolved in 48 ml of methanol and 2.6 ml of water, mixed with 833 mg of sodium metaperiodate and stirred for two days at room temperature and for one hour at 50° C. For working-up, the reaction mixture is added to semi-saturated sodium chloride solution, extracted three times with methylene chloride, washed with saturated sodium chloride solution, dried on magnesium sulfate and concentrated by evaporation in a vacuum. The residue is purified by preparative column chromatography with hexane/acetone as an eluant. 929 mg of (S)-tert-butyl-2-β{[4-(trifluoromethyl)phenyl]-sulfinylmethyl}pyrrolidine-1-carboxylate is obtained.

b) (S)-2-{[4-(Trifluoromethyl)phenyl]sulfinylmethyl}pyrrolidine 920 mg of (S)-tert-butyl-2-{[4-(trifluoromethyl)phenyl]-sulfinyl-methyl}pyrrolidine-1-carboxylate is added to a mixture, cooled to 0° C., that consists of 7.2 ml of trifluoroacetic acid, 0.22 ml of triisopropylsilane and 0.30 ml of water, heated for a short time to room temperature until the educt is dissolved and then stirred for 30 minutes at 0° C. Then, the reaction is set at pH 10 with lot potassium hydroxide solution, extracted three times with methylene chloride, washed with saturated sodium chloride solution, dried on magnesium sulfate and concentrated by evaporation in a vacuum. 549 mg of (S)-2-{[4-(trifluoromethyl)-phenyl] sulfinyl}pyrrolidine is obtained as a crude product.

What is claimed is:

1. An 11β-substituted estratriene of formula I

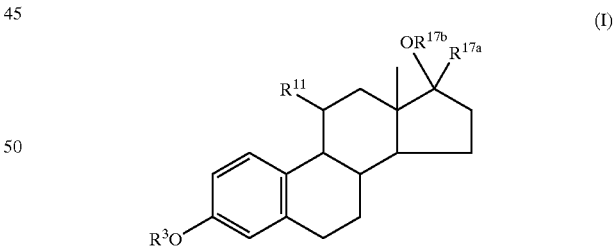

in which $R^3$ means a hydrogen atom, a hydrocarbon radical with up to 8 carbon atoms or a radical of partial formula $R^{3'}$—C(O)—, in which $R^{3'}$ means a hydrogen atom or a hydrocarbon radical with up to 8 carbon atoms or a phenyl radical, $R^{11}$ means a radical of formula —A—B—Z—$R^{20}$, in which A stands for a direct bond, and B stands for a straight-chain or branched-chain alkylene, alkenylene or alkinylene group with 4, 5 or 6 carbon atoms, Z stands for —NR$^{21}$- and R$^{21}$ stands for a C$_1$–C$_3$ alkyl group,
  whereby R$^{20}$ means
    a hydrogen atom,
    a straight-chain or branched-chain alkyl, alkenyl or alkinyl group with up to 10 carbon atoms,
    —D—C$_n$F$_{2n+1}$, whereby D is a straight-chain or branched-chain alkylene, alkenylene or alkinylene group with up to 8 carbon atoms and n is an integer from 1 to 8,
    —D-aryl, whereby D has the already indicated meaning, and aryl stands for a phenyl, 1- or 2-naphthyl radical or a heteroaryl radical that is optionally substituted in one or two places,
    —L—CH=CF—C$_p$F$_{2p+1}$, whereby L is a straight-chain or branched-chain alkylene, alkenylene or alkinylene group with up to 7 carbon atoms and p is an integer from 1 to 7,
    whereby in the three cases above in D or L, a methylene group can be replaced by a sulfur atom, a sulfone group or a sulfoxide group,
    —D—O—(CH$_2$)q-aryl, whereby D and aryl have the already indicated meanings, and q is 0, 1, 2 or 3,
    —D—O—(CH$_2$)$_r$—C$_n$F$_{2n+1}$, whereby D and n have the already indicated meanings, and r stands for an integer from 1 to 5,
      whereby in addition in all relevant cases above, R$^{21}$ together with D with the inclusion of the nitrogen atom can then form a pyrrolidine ring that is substituted in 2- or 3-position,
  or
    R$^{20}$ and R$^{21}$ with the nitrogen atom to which they are bonded form a saturated or unsaturated heterocyclic compound with 5 or 6 chain links, which optionally contains one or two additional heteroatoms, selected from nitrogen, oxygen and sulfur, and optionally is substituted, and
R$^{17a}$ in α- or β-position means a hydrogen atom, a C$_{1-5}$ alkyl, a C$_{2-5}$ alkenyl or a C$_{2-5}$ alkinyl group or a trifluoromethyl group, or together with the radical OR$^{17b}$ means a keto-oxygen atom, and
R$^{17b}$ means a hydrogen atom or a radical of partial formula R$^{17'}$—C(O)—, in which
R$^{17'}$ means a hydrogen atom or a hydrocarbon radical with up to 8 carbon atoms.

2. An 11β-substituted estratriene according to claim 1, in which R$^3$ is a hydrogen atom.

3. An 11β-substituted estratriene according to claim 1, in which R$^3$ is a benzoyl radical.

4. An 11β-substituted estratriene according to claim 1, in which R$^{17b}$ is a hydrogen atom.

5. An 11β-substituted estratriene according to claim 1, in R$^{11}$ is selected from the group of the following side chains
—(CH$_2$)$_5$N(CH$_3$)—(CH$_2$)$_3$—S—(CH$_2$)$_3$C$_2$F$_5$,
—(CH$_2$)$_5$NH—(CH$_2$)$_3$—S—(CH$_2$)$_3$C$_2$F$_5$,
—(CH$_2$)$_5$N(CH$_3$)—(CH$_2$)$_3$—S—CH$_2$—2-Pyridyl,
—(CH$_2$)$_5$N(CH$_3$)—(CH$_2$)$_3$—SO—CH$_2$—2-Pyridyl,
—(CH$_2$)$_5$N(CH$_3$)—(CH$_2$)$_3$—S—CH$_2$-p-CF$_3$-Phenyl,
—(CH$_2$)$_5$N(CH$_3$)—(CH$_2$)$_3$—SO—CH$_2$-p-CF$_3$-Phenyl,
—(CH$_2$)$_5$-[2-pyrrolidine-1-yl]—CH$_2$—S-p-CF$_3$-Phenyl,
—(CH$_2$)$_5$-[2-pyrrolidine-1-yl]—CH$_2$—SO-p-CF$_3$-Phenyl,
—(CH$_2$)$_5$N(CH$_3$)(CH$_2$)$_3$C$_2$F$_5$,
—(CH$_2$)$_5$N(CH$_3$)(CH$_2$)$_6$C$_2$F$_5$,
—(CH$_2$)$_5$N(CH$_3$)(CH$_2$)$_7$C$_2$F$_5$,
—(CH$_2$)$_5$N(CH$_3$)(CH$_2$)$_8$C$_2$F$_5$,
—(CH$_2$)$_6$N(CH$_3$)(CH$_2$)$_6$C$_2$F$_5$,
—(CH$_2$)$_6$N(CH$_3$)(CH$_2$)$_7$C$_2$F$_5$,
—(CH$_2$)$_6$N(CH$_3$)(CH$_2$)$_8$C$_2$F$_5$,
—(CH$_2$)$_5$N(CH$_3$)(CH$_2$)$_2$C$_4$F$_9$,
—(CH$_2$)$_5$N(CH$_3$)(CH$_2$)$_3$C$_6$F$_{13}$,
—(CH$_2$)$_5$N(CH$_3$)(CH$_2$)$_3$C$_8$F$_{17}$,
—(CH$_2$)$_5$N(CH$_3$)(CH$_2$)$_6$C$_4$F$_9$,
—(CH$_2$)$_5$N(CH$_3$)(CH$_2$)$_6$C$_6$F$_{13}$,
—(CH$_2$)$_5$N(CH$_3$)(CH$_2$)$_6$C$_8$F$_{17}$,
—(CH$_2$)$_5$N(CH$_3$)H,
—(CH$_2$)$_5$N(CH$_3$)(CH$_2$)$_9$H,
—(CH$_2$)$_5$N(CH$_3$)CH$_2$CH=CF—C$_2$F$_5$,
—(CH$_2$)$_5$N(CH$_3$)CH$_2$CH=CF—C$_3$F$_7$,
—(CH$_2$)$_5$N(CH$_3$)CH$_2$CH=CF—C$_5$F$_{11}$,
—(CH$_2$)$_5$N(CH$_3$)CH$_2$CH=CF—C$_7$F$_{15}$,
—(CH$_2$)$_5$-1-Pyrrolidinyl,
—(CH$_2$)$_5$N(CH$_3$)(CH$_2$)$_3$OPhenyl,
—(CH$_2$)$_5$N(CH$_3$)(CH$_2$)$_3$OBenzyl,
—(CH$_2$)$_5$N(CH$_3$)(CH$_2$)$_3$O(CH$_2$)$_3$C$_2$F$_5$,
—(CH$_2$)$_5$N(CH$_3$)(CH$_2$)$_3$CH(CH$_3$)$_2$,
—(CH$_2$)$_5$N(CH$_3$)(CH$_2$)$_3$-Pyridyl,
—(CH$_2$)$_5$N(CH$_3$)(CH$_2$)$_3$-Phenyl,
—(CH$_2$)$_5$N(CH$_3$)(CH$_2$)$_3$-p-Tolyl,
—(CH$_2$)$_5$N(CH$_3$)(CH$_2$)$_3$-p-ethoxyphenyl,
—(CH$_2$)$_5$N(CH$_3$)(CH$_2$)$_3$-p-Tolyl,
—(CH$_2$)$_5$N(CH$_3$)(CH$_2$)$_3$-p-Chlorophenyl, or
—(CH$_2$)$_5$N(CH$_3$)(CH$_2$)$_3$—O—CH$_2$-Phenyl.

6. A compound of claim 1 which is
11β-[5-(methyl{3-[(4,4,5,5,5-pentafluoropentyl)sulfanyl]-propyl}amino)pentyl]estra-1,3,5(10)-triene-3,17β-diol,
11β-(5-{3-[(4,4,5,5,5-pentafluoropentyl)sulfanyl]-propylamino}pentyl]estra-1,3,5(10)-triene-3,17β-diol,
11β-[5-(methyl{3-[(2-pyridylmethyl)sulfanyl]propyl}-amino)pentyl]estra-1,3,5(10)-triene-3,17β-diol,
11β-(5-{methyl{3-[(2-pyridylmethyl)sulfonyl}propyl}amino)pentyl]estra-1,3,5(10)-triene-3,17β-diol,
11β-[5-(methyl{3-[4-trifluoromethyl)benzylsulfanyl]-propyl}-amino)pentyl]estra-1,3,5(10)-triene-3,17β-diol,
11β-[5-(methyl{3-[4-(trifuoromethyl)benzylsulfinyl]propyl}-amino)pentyl]estra-1,3,5(10)-triene-3,17β-diol,
11β-{5-[(2S)-2-{[4-(trifluoromethyl)phenyl]sulfanyl-methyl}pyrrolidine-1-yl]pentyl}estra-1,3,5(10)-triene-3,17β-diol,
11β-{5-[(2S)-2-{[4-(trifluoromethyl)phenyl]sulfinyl-methyl}pyrrolidine-1-yl]pentyl}estra-1,3,5(10)-triene-3,17β-diol,
11β-{5-[methyl-(8,8,9,9,9-pentafluoro-nonyl)amino]-pentyl}-estra-1,3,5(10)-triene-3,17β-diol,
11β-{5-[methyl-nonyl-amino]pentyl}-estra-1,3,5(10)-triene-3,17β-diol,
11β-{5-[methyl-(9,9,10,10,10-pentafluoro-decyl)-amino]-pentyl{-estra-1,3,5(10)-triene-3,17β-diol,
11β-β{6-[methyl-(8,8,9,9,9-pentafluoro-nonyl)-amino]-hexyl}-estra-1,3,5(10)-triene-3,17β-diol,
11β-{6-[methyl-(9,9,10,10,10-pentafluoro-decyl)amino]-hexyl}-estra-1,3,5(10)-triene-3,17β-diol, 11β-[5-(methyl-amino)-pentyl]-estra-1,3,5(10)-triene-3,17β-diol, 11β-(5-pyrrolidine-1-yl-pentyl)-estra-1,3,5(10)-triene-3,17β-diol, 11β-{5-[methyl-(4,4,5,5,5-pentafluoro-pentafluoro-pentyl)-amino}pentyl}-estra-1,3,5(10)-triene-3,17β-diol, 11β-{5-[methyl-(4,4,5,5,6,6,7,7,8,8,9,9,9-tridecafluoro-nonyl)-amino]-pentyl}-estra-1,3,5(10)-triene-3,17β-diol, 11β-{5-[(4,4,5,5,6,6,7,7,8,8,9,9,10,10,11,11,11-heptadecafluoro-undecyl)-methyl-amino]-pentyl}-estra-1,3,5(10)-triene-3,17β-diol, 11β-{5-[methyl-(3,3,4,4,5,5,6,6,6-nonafluoro-hexyl)-amino]-pentyl}-estra-1,3,5(10)-triene-3,17β-diol, 11β-{-[methyl-(7,7,8,8,8-pentafluoro-octyl)-amino]-pentyl}-estra-1,3,5(10)-triene-3,17β-diol, 11β-{6-[methyl-(7,7,8,8,8-pentafluoro-octyl)-amino]-hexyl}-estra-1,3,5(10)-triene-3,17β-diol, 11β-{5-[methyl-(7,7,8,8,9,9,10,10,10-nonafluoro-decyl)-amino]-pentyl}-estra-1,3,5(10)-triene-3,17β-diol, 11β-{5-[methyl-(7,7,8,8,9,9,10,10,11,11,12,12,12-tridecafluoro-dodecyl)-amino]-pentyl}-estra-1,3,5(10)-triene-3,17β-diol, 11β-{5-[(7,7,8,8,9,9,10,10,11,11,12,12,13,13,14,14,14-heptadecafluoro-tetradecyl)-methyl-amino]-pentyl}-estra-1,3,5(10)-triene-3,17β-diol, 11β-{5-[(3,4,4,5,5,5-hexafluoro-pent-2-enyl)-methyl-amino)-pentyl}-estra-1,3,5(10)-triene-3,17β-diol, 11β-{5-[(3,4,4,5,5,6,6,7,7,8,8,8-dodecafluoro-oct-2-enyl)-methyl-amino]-pentyl}-estra-1,3,5(10)-triene-3,17β-diol, 11β-{5-[(3,4,4,5,5,6,6,7,7,8,8,9,9,10,10,10-hexadecafluoro-dec-2-enyl)-methyl-amino}-pentyl}-estra-1,3,5(10)-triene-3,17β-diol, 11β-{5[methyl(3-phenoxy-propyl)-amino]pentyl}-estra-1,3,5(10)-triene-3,17β-diol, 11β-{5-[(3-benzyloxy-propyl)-methyl-amino]-pentyl}-estra-1,3,5(10)-triene-3,17β-diol, 11β-{5-{N-methyl-N-3-(4,4,5,5,5-pentafluoropentyloxy)-propylamino]-pentyl}-estra-1,3,5(10)-triene-3,17β-diol, 11β-{5-[methyl-2-p-tolyl-ethyl)-amino]-pentyl}-estra-1,3,5(10)-triene-3,17β-diol, 11β-(5-{[2-(4-ethoxy-phenyl)-ethyl]-methyl-amino}-pentyl)-estra-1,3,5(10)-triene-3,17β-diol, 11β-{5-[methyl-(3-phenyl-propyl)-amino]-pentyl}-estra-1,3,5(10)-triene-3,17β-diol, 11β-{-[methyl-(3-pyridin-3-yl-propyl)-amino]-pentyl}-estra-1,3,5(10)-triene-3,17β-diol, 11β-{5-[methyl-(3-ptolyl-propyl)-amino]-pentyl}-estra-1,3,5(10)-triene-3,17β-diol, 11β-(5-{[3-(4-chloro-phenyl)-propyl]-methyl-amino}-pentyl)-estra-1,3,5(10)-triene-3,17β-diol, 11β-(5-{[3-(4-ethoxy-phenyl)-propyl]-methyl-amino}-pentyl)-estra-1,3,5(10)-triene-3,17β-diol, or 11β{5[methyl-(4-methyl-pentyl)-amino]-pentyl}-estra-1,3,5(10)-triene-3,17β-diol.

7. A pharmaceutical agent comprising a 11β-long-chain-substituted estratriene according to claim 1.

8. A pharmaceutical composition comprising at least one compound of formula I according to claim 1 and a pharmaceutically compatible vehicle.

9. An 11β-substituted estratriene according to claim 1, wherein $R_{17a}$ is a methyl, an ethenyl or an ethynyl.

10. An 11β-substituted estratriene according to claim 1, wherein $R^{17a}$ is in the α-position.

11. A method of providing an antiestrogenic action comprising administration an effective amount of a compound according to claim to a patient in need thereof.

12. A method of treating tumors comprising administrating an effective amount of a compound according to claim 1.

13. A method of treating osteoporosis, or pre-, peri- or post-menopause comprising administrating an effective amount of a compound according to claim 1 to a patient in need thereof.

14. A method of providing hormone replacement therapy comprising administering an effective amount of a compound according to claim 1 to a patient in need thereof.

15. A method of treating breast cancer, endometrial cancer, prostate cancer, prostatic hyperplasia, anovulatory infertility, melanoma, male hair loss, diffuse alopecia, hirsutism, endometriosis, or endometrial carcinomas by administrating an effective amount of a compound according to claim 1 to a patient in need thereof.

* * * * *